United States Patent [19]
Saltzman

[11] 3,969,626
[45] July 13, 1976

[54] METHOD AND APPARATUS FOR DETECTING TOTAL REDUCED SULFUR

[75] Inventor: Robert S. Saltzman, Wilmington, Del.

[73] Assignee: E. I. Du Pont de Nemours and Company, Wilmington, Del.

[22] Filed: Feb. 18, 1975

[21] Appl. No.: 550,852

[52] U.S. Cl. .................................. 250/344; 250/343
[51] Int. Cl.² .......................................... G01J 1/00
[58] Field of Search ............ 250/343, 373, 377, 346

[56] References Cited
UNITED STATES PATENTS

| | | | |
|---|---|---|---|
| 3,013,153 | 12/1961 | Fisher et al. | 250/373 |
| 3,449,565 | 6/1969 | Barringer | 250/373 |
| 3,696,247 | 10/1972 | McIntosh et al. | 250/343 |
| 3,835,322 | 9/1974 | Komatsuru | 250/343 |
| 3,845,309 | 10/1974 | Helm et al. | 250/373 |

Primary Examiner—Alfred E. Smith
Assistant Examiner—B. C. Anderson

[57] ABSTRACT

Disclosed herein is a method for detecting total reduced sulfur in a sample gas, comprising the steps of: introducing sample gas into a sample cell, passing detecting radiation of a wavelength between about 250 and about 330 nm. through the sample gas, detecting the intensity of the detecting radiation passing through the sample gas, introducing an oxygen-containing gas into the cell to form a gas mixture with a sample gas, heating the gas mixture to a temperature above about 200°C., passing the detecting radiation through the heated gas mixture in the cell, and detecting the intensity of the detecting radiation passing through the gas mixture. The difference between the intensity of the detecting radiation passing through the gas mixture and that passing through the sample gas alone is indicative of the total reduced sulfur content of the sample gas. An apparatus to practice the above method is also disclosed.

13 Claims, 5 Drawing Figures

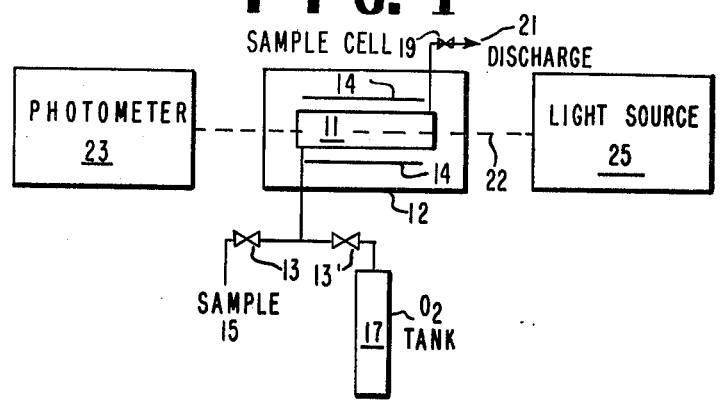
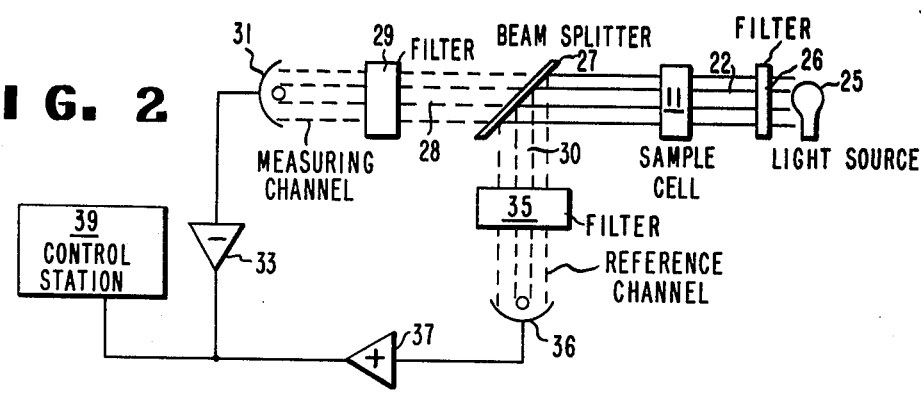
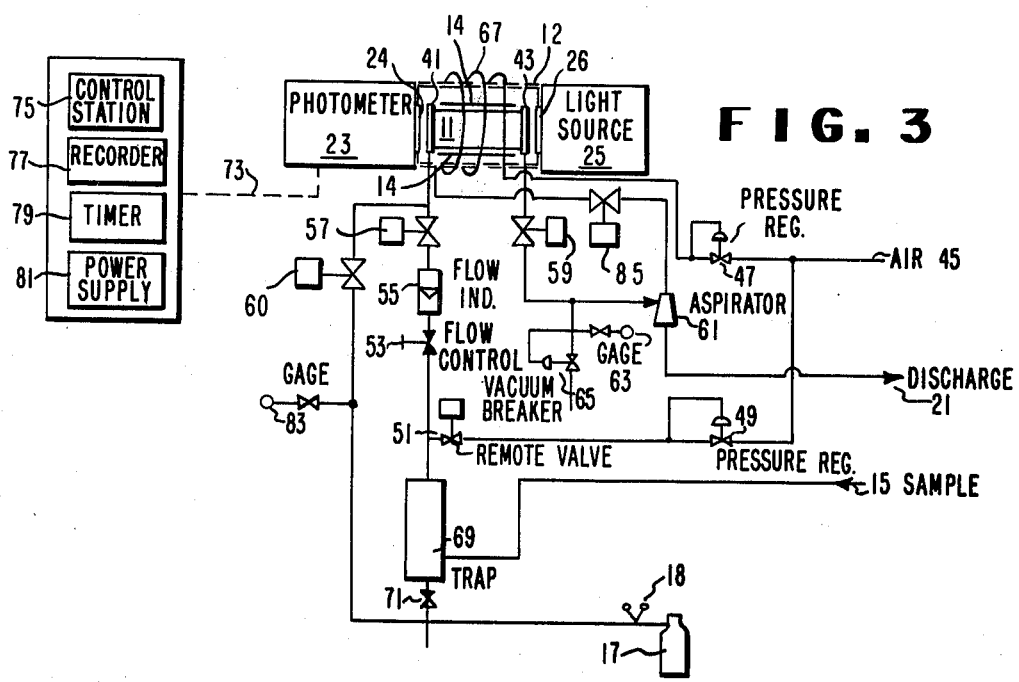

METHOD AND APPARATUS FOR DETECTING TOTAL REDUCED SULFUR

BACKGROUND OF THE INVENTION

1. Field of the Invention

The present invention relates to a method and apparatus useful for detecting total reduced sulfur in a sample gas. More particularly, it relates to a method and apparatus for detecting total reduced sulfur in which the sample gas is heated to oxidize the total reduced sulfur to $SO_2$ and the $SO_2$ content of the sample is measured prior to and after the heating step.

2. Discussion of the Prior Art

The total reduced sulfur content of a gas includes sulfur vapor, hydrogen sulfide, mercapto compounds, other organic compounds containing sulfur, and a variety of other substances; all of which are considered pollutants by the Environmental Protection Agency. It is known that these substances can be oxidized to $SO_2$ by contacting them with oxygen at elevated temperatures. It is also known that $SO_2$ absorbs radiation of a wavelength between 250 and 330 nm. Despite this knowledge, however, no simple, sensitive effective method or apparatus has been developed to measure the total reduced sulfur content of a gas, independent of its $SO_2$ content.

The reason for this is simply that unless a reference reading is taken prior to heating the sample gas, there is no way to distinguish between the total reduced sulfur and the $SO_2$ content of the sample gas. Such a reference reading is difficult to make because the conditions necessary for the reference reading are significantly different from those necessary for the total reduced sulfur reading. For one thing, the total reduced sulfur reading must be made at an elevated temperature, whereas the reference measurement must be made at a much lower temperature. Furthermore, unless oxygen is actually added to the sample gas, complete conversion of the total reduced sulfur components of the sample gas may not occur, particularly at high total reduced sulfur concentration.

Dual flow cell techniques have been used to avoid this problem, but the new problem of balancing the flows to each cell in such systems has been such that the sensitivity and accuracy of the dual cell system is lower than required for many applications. Unless a single cell, in situ method is used, highly accurate total reduced sulfur measurement can not be made without extreme difficulty, particularly on sample gases containing low total reduced sulfur concentrations in the presence of high $SO_2$ concentration. Because of the temperature requirements placed on single cell techniques, however, in situ techniques have been considered too slow and have been avoided.

It has now been found that an in situ measurement is practical; that excess oxygen can be added to a closed, in situ system; and that the temperature of the receptacle in which the sample gas is contained can be cycled rapidly enough to make repeditive measurements of the total reduced sulfur content of a sample by first taking a reference measurment, adding an oxygen containing gas, then heating the gas to the elevated temperature, and finally, cooling the system so that the entire process can be repeated within a short time interval. It has also been found that such a cyclic process yields accurate results free of contamination by the previously measured sample gas. The high temperature and the consequent conversion of the reduced sulfur components to $SO_2$ appears to have a self-cleaning effect on the system.

SUMMARY OF THE INVENTION

This is accomplished by a method comprising the steps of:

a. introducing sample gas into a sample cell;
b. passing detecting radiation of a wavelength between about 250 to about 330 nm. through the sample gas in the cell, the detecting radiation being of a wavelength strongly absorbed by $SO_2$;
c. measuring the intensity of the detecting radiation passing through the sample gas;
d. sealing the sample gas in the cell;
e. introducing an oxygen-containing gas into the cell to form a gas mixture with the sample gas, the gas mixture being retained in the cell;
f. thereafter heating the gas mixture to a temperature above about 200°C.;
g. passing the detecting radiation through the heated gas mixture in the cell; and
h. measuring the intensity of the detecting radiation passing through the gas mixture, the difference between the intensity of the detecting radiation passing through the gas mixture and that passing through the sample gas alone being indicative of the total reduced sulfur content of the sample gas.

In a preferred embodiment, the sample cell is a flow cell and:

a. the step of introducing sample gas into the cell is accomplished by allowing the sample gas to pass continuously through the cell; and
b. the step of introducing an oxygen-containing gas into the cell to form a gas mixture is accomplished by first closing one end of the flow cell, then closing off the remaining end of the flow cell to retain the sample gas in the flow cell; and then introducing the oxygen-containing gas into the cell to form a gas mixture.

In still more preferred embodiments, the oxygen-containing gas is substantially pure oxygen, the gas mixture is heated to a temperature above about 500°C., and the entire process is a repeditive process comprising the further steps of purging the sample cell of the gas mixture, cooling the cell, and repeating the procedure set forth above.

The apparatus for determining the amount of total reduced sulfur in the sample gas comprises:

a. a flow cell having windows transparent at least to radiation of a wavelength in the range of about 250 to about 330 nm.;
b. an inlet for introducing sample gas into the cell;
c. means to form the cell into a gas-tight cell retaining the sample gas;
d. an inlet for introducing an oxygen-containing gas into the cell to form a gas mixture;
e. a radiation source disposed adjacent to one of the windows in the cell for passing radiation of a wavelength in the range of about 250 to about 330 nm. through the cell;
f. a detector disposed adjacent to another of the windows in the cell, the detector being responsive to the intensity of radiation passing through the cell; and
g. a heater associated with the cell to raise the temperature of the gas mixture in the cell to above about 200°C. in a time less than about 2 minutes.

In a preferred embodiment, the cell is a quartz cell and the means to heat the cell is an infrared heater capable of heating the cell to a temperature above about 500°C. in a time less than about 2 minutes.

BRIEF DESCRIPTION OF THE DRAWINGS

The present invention can most easily be described by reference to the figures in which:

FIG. 1 is a schematic diagram of one embodiment of an apparatus for practicing the present invention;

FIG. 2 is an illustration of a preferred photometer for use in the present invention;

FIG. 3 shows a detailed representation of a preferred embodiment of an apparatus of the present invention;

DETAILED DESCRIPTION OF THE INVENTION

Figure 5:
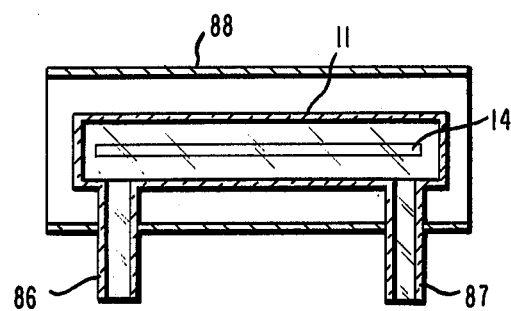
FIG. 5 is a cross-sectional view taken along the line 5—5 of FIG. 4.

The present invention relates to a system in which the total reduced sulfur content of a gas is photometrically determined. This is accomplished using ultraviolet radiation having a wavelength in the range of about 250 to about 330 nm., to detect the $SO_2$ content of the sample gas both before and after its reduced sulfur content has been converted to $SO_2$. $SO_2$ absorbs radiation at a number of known wavelengths in the range set forth above; e.g., 280 nm., 289 nm., 297 nm., and 302 nm. These wavelengths can be obtained from a mercury discharge lamp. Other suitable wavelengths, well known to those skilled in the art, can be used.

After an initial $SO_2$ reading, the sample gas is combined with an oxygen-containing gas, preferably substantially pure oxygen, to convert the reduced sulfur content of the gas to $SO_2$ and render it highly absorbing to ultraviolet radiation. To accomplish this conversion, the sample gas is raised to a temperature of above about 200°C. At 200°C., it may take 10 minutes or more to convert 95% of the reduced sulfur in the sample cell to $SO_2$. Therefore, higher temperatures, i.e., above about 500°C., are preferred because of the increased conversion rate. At about 500°C., it takes less than 2 minutes to reproducibly accomplish such conversion.

FIG. 1 shows the basic components of an apparatus to accomplish the photometric determination of the total reduced sulfur content of the gas according to the present invention. Sample gas from sample source 15 is introduced through the three-way valve 13 into sample cell 11 which is contained within compartment 12. In one embodiment of the present invention, compartment 12 may be a heated compartment, but it is preferred to heat the sample cell directly by means of an infrared heater in close association with the sample cell, as indicated by 14.

Sample cell 11 is a gas tight sample cell which can withstand pressures of at least 2 atmospheres, preferably 5 atmospheres, and temperatures of at least 500°C., preferably 1000°C. The sample may come from any desired source, such as an industrial stack. Normally, the sample cell is a flow cell and the sample gas passes through it continuously, via valve 19 and discharge 21, until valve 19 is closed to retain a specific amount of the sample gas within the cell 11.

After valve 19 is closed, valve 13 is closed and valve 13' is opened to introduce oxygen, or any other suitable oxygen-containing gas, such as air, from tank 17 into sample cell 11. The measurement of the $SO_2$ content of the gas can also be made at this point or at any prior point in time.

Radiation source 25, which is disposed adjacent to one of the windows in cell 11, is provided to pass radiation 22 through sample cell 11. The transmitted radiation is detected by a detector 23, which is located adjacent to the other window in cell 11. The radiation source is generally a light source, and the radiation detector is generally a photometer. This system is used to measure the intensity of the detecting radiation which passes through the sample gas and provides an indication of the $SO_2$ content of the gas.

After the $SO_2$ content of the gas has been measured, sample cell 11 and the gas mixture contained within it are heated to a temperature above about 200°C. by a heater 14, which in the preferred embodiment, is an infrared heater. After a time sufficient to allow conversion of all the reduced sulfur in the sample gas to $SO_2$, detecting radiation is again passed through the sample cell from light source 25 to photometer 23 and a measurement of the intensity of the detecting radiation is made. The difference between the intensity of the detecting radiation passing through the gas mixture and that passing through the sample gas alone is indicative of the total reduced sulfur content of the sample gas.

Figure 4:
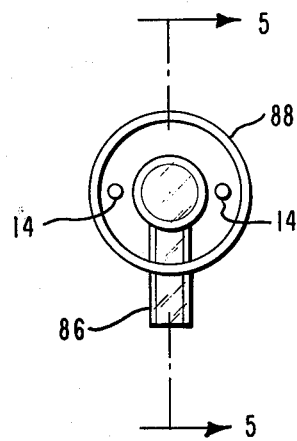
FIG. 4 is an enlarged end view of one embodiment of the sample cell and associated heater used in the present invention.

A preferred embodiment of the sample cell and associated heater is shown in FIGS. 4 and 5. In these figures, sample cell 11 is a quartz sample cell having an external diameter of about 1 inch, and a length ranging from 20 to 100 cm., depending on application. The quarter inch inlet and outlet tubes 86 and 87 are coupled to the rest of the system by suitable high temperature connectors. The sample cell is wrapped or otherwise encased, except at its ends, with a suitable high temperature sheet insulation 88, rated to about 1200°C. Located between the insulation and sample cell are two infrared quartz lamps 14, equivalent to Type QH1600T3/7 General Electric quartz heat lamp.

FIG. 2 shows one suitable photometer for use with the present invention. This radiation source comprises means to generate detecting radiation and means to generate reference radiation. In the present embodiment, both are combined into one light source 25 which may be of any suitable type, although a mercury lamp is preferred. An optical filter 26 may be provided to filter out undesirable radiation from the light beam. The light then passes through sample cell 11 wherein it is absorbed by the $SO_2$ and scattered by particulate matter and mists. After exiting the cell 11, light beam 22 passes to a detector responsive to the radiation passing through the cell. In this embodiment, the detector is a photometer 23. Upon entering the photometer, light beam 22 is divided into two components by beam splitter 27, which in the case illustrated, is a semitransparent mirror. A portion of the beam 28 passes through filter 29 which blocks all but the detecting radiation (which is responsive to both $SO_2$ absorption and scattered radiation). Phototube 31 detects this radiation and generates an electrical signal proportional to its intensity. Its output is positively amplified by a logarithmic amplifier 33. The second portion 30 of the beam from beam splitter 27 passes through filter 35 which excludes all but the reference wavelength of radiation. This reference radiation responds equally to the scattering in the cell as does the detecting radiation, but it is weakly absorbed by $SO_2$; i.e., it is either not absorbed or relatively less absorbed. The radiation passes through filter 35 to phototube 36 which generates an electrical signal proportional to its intensity. The output of phototube 36 is negatively amplified by logarithmic amplifier 37. The output of negative amplifier 37 effectively subtracts the scattering of radiation in the sample cell from the output of the detecting phototube 31, and, thus, allows only a signal indicative of the $SO_2$ absorption to reach control station 39. This data is then available for further use.

FIG. 3 depicts a preferred embodiment of the present invention. Photometer 23 and light source 25 are shown with windows 24 and 26, respectively. These windows are preferably of quartz. Sample cell 11 has windows 41 and 43 (also preferably of quartz) and it is located within compartment 12. The sample cell itself is preferably made from quartz, but it can be made from any other suitable material which can be heated rapidly to a temperature above 200°C. and cooled rapidly. In association with sample cell 11 is a heater element 14, which in the preferred embodiment, is an infrared heater capable of raising the temperature of the sample cell and the gas mixture within it to a temperature above 200°C. in a very short period of time.

Power supply 81 powers light source 25, photometer 23, and remote valves 51, 57, 59, 60 and 85. Timer 79 controls the functioning of these valves. Control station 75, recorder 77, timer 79, and power supply 81 are connected to the rest of the system by electrical interconnection 73.

Air is supplied under pressure from a source 45. This high pressure serves three purposes. First, it continuously provides air under pressure to drive aspirator 61, which is used to create a vacuum in the line leading to the sample cell. The sample cell pressure is controlled by vacuum breaker 65, and the pressure of the air supplied to aspirator 61 is regulated by pressure regulator 47. After passing through aspirator 61, the air is discharged through port 21.

The second function of the air provided from source 45 occurs during the apparatus' first cycle of operation. During the cycle, valve 51 is opened to admit air under pressure (regulated by pressure regulator 49) into the line connecting sample cell 11 to sample source 15. A portion of this air stream is used to backflush the sample line through trap 69 to sample source 15. This cleans the line in preparation for the next measurement. During this first cycle, valve 57 is opened to permit the other portion of the air stream to flow into the sample cell 11, while valve 59 is open to purge sample cell 11 and force its contents through aspirator 61 and out discharge port 21. In this manner, the sample cell and its connections are also cleansed. Since there is no sample in sample cell 11 while the air is flowing through it, during the first cycle, the photometer output can be zeroed by passing detecting radiation through the cell. After cell 11 and its connecting lines are cleansed, valve 51 closes and isolates the line connecting sample cell 11 and sample 15 from the air (although, of course, the air continues to operate aspirator 61).

The third function of air from source 45 is to aid in cooling the sample cell and any gas contained in it. Air is provided from pressure regulator 47 to aspirator 61 through heat exchange 67 and valve 85. The heat exchange is coiled around, or in some way associated with, the sample cell and the air passing through the heat exchange acts to cool the cell. During the heating cycle, valve 85 is activated to shut off the flow of air from source 45. This allows the heating of sample cell 11 to occur as rapidly as possible. Valve 85 opens as soon as cooling is required.

The closing of valve 51 begins the second cycle. During this cycle, valve 57 allows the passage of gas through one side of the sample cell 11 and out the other side through valve 59, aspirator 61, and discharge port 21. Air from source 45, which continues to pass through aspirator 61, creates a slight vacuum in the sample cell and its connecting lines. A vacuum of about 3 inches of mercury at the aspirator 61 is convenient. This slight vacuum in the sample cell (without the backflushing air pressure) urges the sample gas from source 15 to flow forward through trap 69, flow controller 53, flow indicator 55, valve 57, sample cell 11, valve 59, aspirator 61, and out discharge port 21. The sample gas passes to trap 69 where liquid or particulate matter that has condensed is removed. Flow indicator 55 need only be occasionally checked to ascertain that flow control 53 is permitting the correct amount of sample to flow into sample cell 11.

Vacuum breaker 65 limits and controls the magnitude of the vacuum within sample cell 11 and its connecting lines, with gauge 63 giving a visual indication of the vacuum. Vacuum breaker 65 bleeds in sufficient air to reduce the vacuum created by aspirator 61 to the desired magnitude. Because the pressure within the sample cell is thus accurately controlled, the amount of sample within the sample cell 11 is also accurately controlled. Accordingly, even when the sample gas is flowing through the sample cell 11, the concentration of $SO_2$ within the sample cell may be accurately determined by light source 25 and photometer 23.

When a sample is within sample cell 11, valve 57 closes in order to isolate the sample within the cell. Three-way valve 59, however, remains open sufficiently long for the pressure (and hence the amount of sample gas) in the sample cell 11 to be regulated and controlled by vacuum breaker 65. Then valve 59 closes and isolates the sample within the sample cell.

During the succeeding third cycle, valve 60 opens to allow oxygen-containing gas from tank 17 to flow through gauge 18, past gauge 83 and through valve 60 into one end of the sample cell 11. Gauge 83 is attached to the line in order to allow for accurate adjustment of the valves 18 on tank 17. After the desired amount of oxygen, usually about 7 psig, has passed into sample cell 11, valve 60 closes off to isolate the mixture of sample gas and oxygen within sample cell 11.

When the total reduced sulfur concentration of the gas is small relative to its $SO_2$ concentration, increased precision can be obtained by electrically suppressing to zero the $SO_2$ reading and changing the range of the recorder to a more sensitive setting before introducing the oxygen-containing gas.

At this point, the temperature of the sample cell is raised to above about 200°C., preferably above about 500°C., by heater 14 and the oxygen and reduced sulfur in the sample gas are allowed to react for a time sufficient to convert all the reduced sulfur content of the gas to $SO_2$. If pure oxygen is used, then lower temperatures will suffice to provide conversion in a reasonable time. A measurement of the intensity of the detecting radiation passing through the gas mixture at this point is then made. The difference between the intensity of the detecting radiation passing through the gas mixture and the intensity of the detecting radiation passing through the sample gas alone is indicative of the total reduced sulfur content of the sample gas. This is usually accomplished by generating an electrical signal proportional to the difference between the intensity of the detecting radiation passing through the gas mixture and the intensity of the detecting radiation passing through the sample gas alone.

In typical operation, the system shown in FIG. 3 is operated as a flow cell. Sample gas flows through the cell, and a reference $SO_2$ reading is taken as described above. The ends of the cell are closed off in order to retain about 0.9 atmospheres of the sample gas. Seven psig of air is then introduced into the cell and the heater is activated for about 30 seconds at which time the cell and retained gas mixture has reached 600°C. Within another 15 seconds, the temperature of the cell and retained gas has peaked at about 700°C. After about 2 minutes, a total reduced sulfur reading is taken, as described above, and the system begins to cool down, aided by the action of heat exchange 67. In about 2–4 minutes, the cell has cooled to about 400°C. at which time the valves isolating the cell are opened and sample gas is allowed to flow through the system. This purges the cell and aids in cooling it down to about 200°C. at which point it is ready for the next cycle.

Typically, sample gases contain 50 to 250 ppm of $SO_2$ and total reduced sulfur concentrations ranging from less than 5 to more than 600 ppm. The system described above is sensitive enough to measure 1 ppm. total reduced sulfur in the presence of 200 ppm. of $SO_2$.

The above description is intended to exemplify only one embodiment of the present invention. A number of modifications apparent to one skilled in the art can be made to the present invention and are intended to be included within the scope of the invention as set forth in the attached claims.

What is claimed is:

1. A method for determining the total reduced sulfur content of a gas comprising the steps of:
   a. introducing a sample of the gas into a sample cell;
   b. passing detecting radiation of a wavelength between about 250 to about 330 nm. through the gas sample in the cell, said detecting radiation being of a wavelength strongly absorbed by $SO_2$;
   c. measuring the intensity of the detecting radiation passing through the gas sample;
   d. sealing the gas sample in the cell;
   e. introducing an oxygen-containing gas into the cell to form a gas mixture containing oxygen and the gas sample, said gas mixture being retained in the cell;
   f. thereafter heating the gas mixture to a temperature above about 200°C. to oxidize the total reduced sulfur in the gas sample;
   g. passing the detecting radiation through the heated gas mixture in the cell; and
   h. measuring the intensity of the detecting radiation passing through the gas mixture; the difference between the intensity of the detecting radiation passing through the gas mixture and that passing through the gas sample alone being indicative of the total reduced sulfur content of the sample gas.

2. The method of claim 1 wherein said cell is a flow cell and wherein:
   a. the step of introducing gas sample into the cell is accomplished by allowing the gas sample to pass continuously through the cell; and
   b. the step of introducing an oxygen-containing gas into the cell to form a gas mixture is accomplished by first closing off one end of the flow cell, then closing off the remaining ends of the flow cell to contain the gas sample in the flow cell, and then introducing the oxygen-containing gas into the cell to form a gas mixture.

3. The method of claim 2 further comprising the steps of purging the sample cell of the gas mixture, cooling the cell, and repeating the procedure set forth in claim 2.

4. The method of claim 3 wherein the step of introducing an oxygen-containing gas into the cell is accomplished by introducing substantially pure oxygen into the cell.

5. The method of claim 4 wherein gas mixture is heated to a temperature above about 500°C.

6. The method of claim 4 further comprising the step of generating an electrical signal proportional to the difference between the intensity of the detecting radiation passing through the gas mixture and the intensity of the detecting radiation passing through the gas sample alone.

7. The method of claim 4 wherein, in addition to detecting radiation, reference radiation is passed through the gas mixture in the cell, said reference radiation being of a wavelength weakly absorbed by $SO_2$.

8. An apparatus for determining the amount of total reduced sulfur in a sample gas comprising:
   a. a flow cell having windows transparent at least to radiation of a wavelength in the range of about 250 to about 330 nm.;
   b. an inlet for introducing a sample of the gas into said cell;
   c. means to form said cell into a gas-tight cell to retain said gas sample;
   d. an inlet for introducing an oxygen-containing gas into said cell to form a gas mixture containing oxygen and the sample gas;
   e. a radiation source disposed adjacent to one of said windows, said radiation source comprising means for passing detecting radiation of a wavelength in the range of about 250 to about 330 nm. through said cell; said detecting radiation being of a wavelength strongly absorbed by $SO_2$;
   f. a detector disposed adjacent to another of said windows, said detector being responsive to the intensity of the radiation passing through said cell;
   g. a heater associated with said cell to raise the temperature of the gas mixture in the cell to above about 200°C. in a time less than about two minutes and allow oxidation of the total reduced sulfur in the gas sample; and
   h. means to generate a signal proportional to the difference between the intensity of the radiation passing through the cell when it contains the gas mixture and the intensity of the radiation passing through the cell when it contains only the gas sample.

9. The apparatus of claim 8 wherein said cell is a quartz sample cell and wherein said means to heat said cell is an infrared heater.

10. The apparatus of claim 9 wherein said means to heat said cell is a means to heat said cell to a temperature above about 500°C. in a time less than about 2 minutes.

11. The apparatus of claim 10 wherein said radiation source further comprises means for passing reference radiation through said cell, said reference radiation being of a wavelength weakly absorbed by $SO_2$, and wherein said means for detecting the intensity of the radiation passing through said cell comprises means for separately detecting the intensity of the detecting radiation and the reference radiation.

12. The apparatus of claim 11 further comprising means for controlling the pressure of the gas mixture within said cell.

13. The apparatus of claim 11 further comprising means to electrically suppress to zero the intensity of the radiation passing through the cell when it contains only the gas sample.

* * * * *